(12) United States Patent
Choy

(10) Patent No.: US 7,347,827 B2
(45) Date of Patent: Mar. 25, 2008

(54) METHOD AND APPARATUS FOR TREATMENT OF MONOFREQUENCY TINNITUS UTILIZING SOUND WAVE CANCELLATION TECHNIQUES

(75) Inventor: Daniel S. J. Choy, New York, NY (US)

(73) Assignee: Tinnitus Care, Inc., New York, NY (US)

( * ) Notice: Subject to any disclaimer, the term of this patent is extended or adjusted under 35 U.S.C. 154(b) by 708 days.

(21) Appl. No.: 10/622,183

(22) Filed: Jul. 16, 2003

(65) Prior Publication Data

US 2004/0059251 A1 Mar. 25, 2004

(51) Int. Cl.
*A61B 5/00* (2006.01)
(52) U.S. Cl. ..................................... 600/559
(58) Field of Classification Search ............... 600/559, 600/300, 25–28; 73/585; 381/124
See application file for complete search history.

(56) References Cited

U.S. PATENT DOCUMENTS

| | | | |
|---|---|---|---|
| 4,049,930 A * | 9/1977 | Fletcher et al. | 381/60 |
| 5,325,872 A | 7/1994 | Westermann | |
| 5,403,262 A | 4/1995 | Gooch | |
| 5,788,656 A | 8/1998 | Mino | |
| 5,795,287 A | 8/1998 | Ball et al. | |
| 5,928,160 A * | 7/1999 | Clark et al. | 600/559 |
| 2002/0177877 A1 | 11/2002 | Choy | |

FOREIGN PATENT DOCUMENTS

| | | |
|---|---|---|
| DE | 10128642 A1 | 6/2001 |
| GB | 2134689 A | 8/1984 |
| GB | 2134689 | 1/1994 |
| WO | 03-051179 A2 | 6/2003 |

* cited by examiner

*Primary Examiner*—Max Hindenburg
*Assistant Examiner*—Fangemonique Smith
(74) *Attorney, Agent, or Firm*—Steven L. Nichols; Rader, Fishman & Grauer PLLC

(57) ABSTRACT

Tinnitus is defined as sound(s) heard by an individual when no external sound is present and often takes the form of a hissing, ringing, chirping or clicking sound which may be either intermittent or constant. According to the American Tinnitus Association, tinnitus affects tens of millions of Americans and many suffer so severely from tinnitus they are not able to function normally on a daily basis. Unfortunately the exact cause or causes of tinnitus are not understood by the medical community and thus many tinnitus sufferers are told by their doctors to "learn to live with it".

In accordance with novel aspects of Applicant's monofrequency tinnitus patient treatment apparatus and process, phase cancellation effects are achieved by utilizing an externally generated sound which is subjectively selected by the monofrequency tinnitus patient to match in both tone and loudness his or her tinnitus sound. This subjectively selected externally generated sound wave which matches in tone and loudness the patient's tinnitus sound, is either (i) sequentially phase shifted through a plurality of phase shift sequence steps totaling at least 180 degrees or (ii) alternatively is directly phase shifted in essentially a single step motion into a 180 degree, out-of-phase reciprocal, canceling relationship with the patient determined tinnitus tone. The sequential steps of the phase shifted tone or the directly phase shifted tone are applied to the tinnitus patient to effect cancellation or diminishment of the patient's tinnitus.

14 Claims, 2 Drawing Sheets

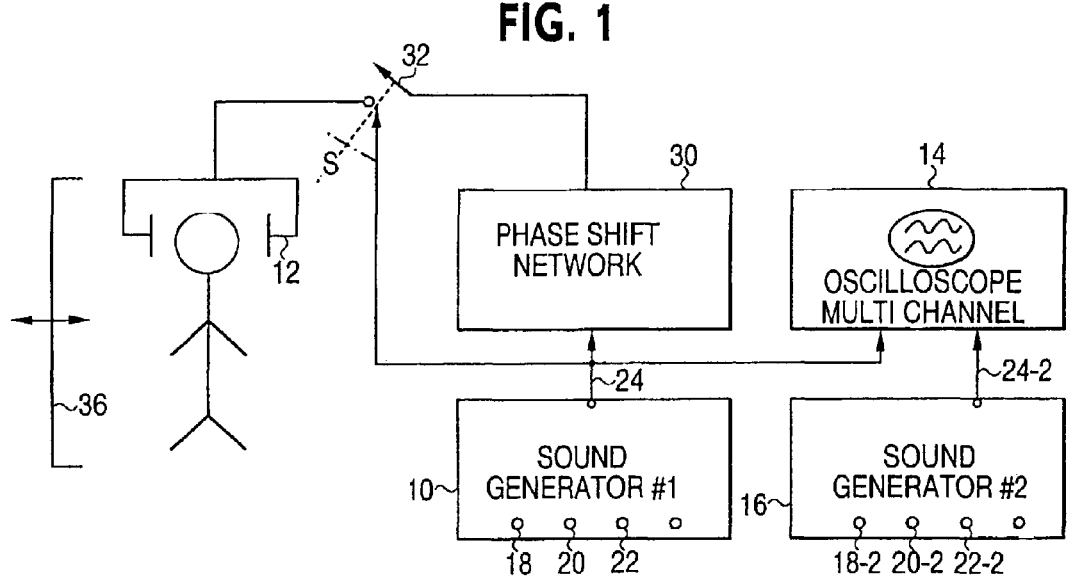
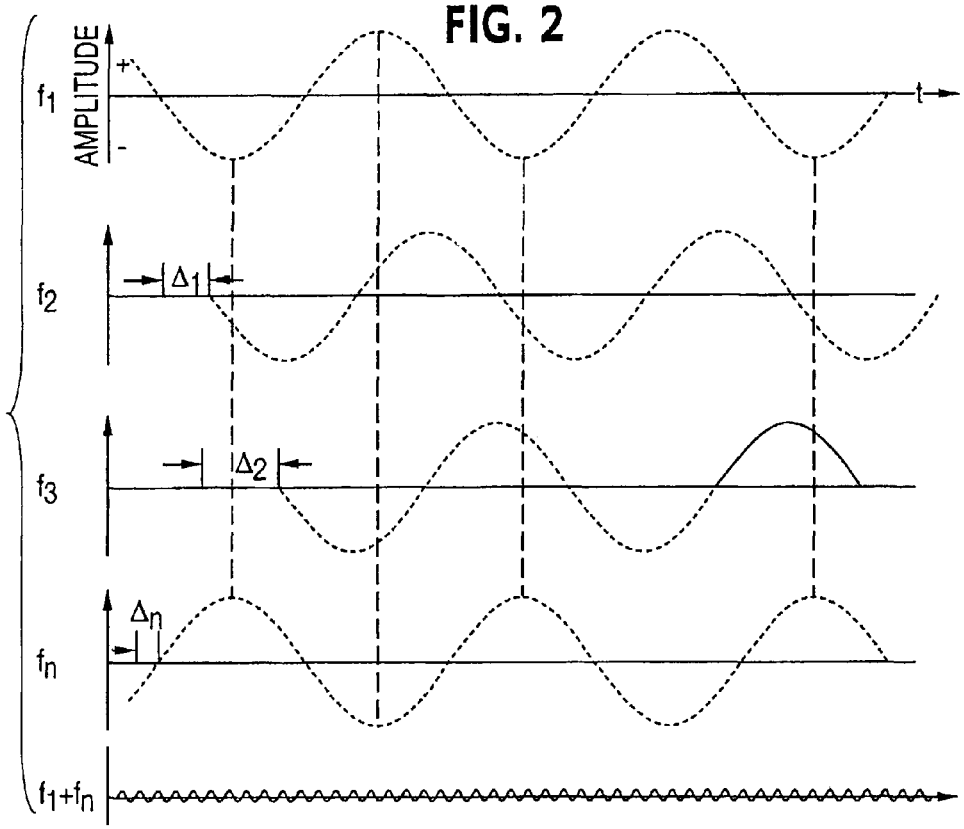

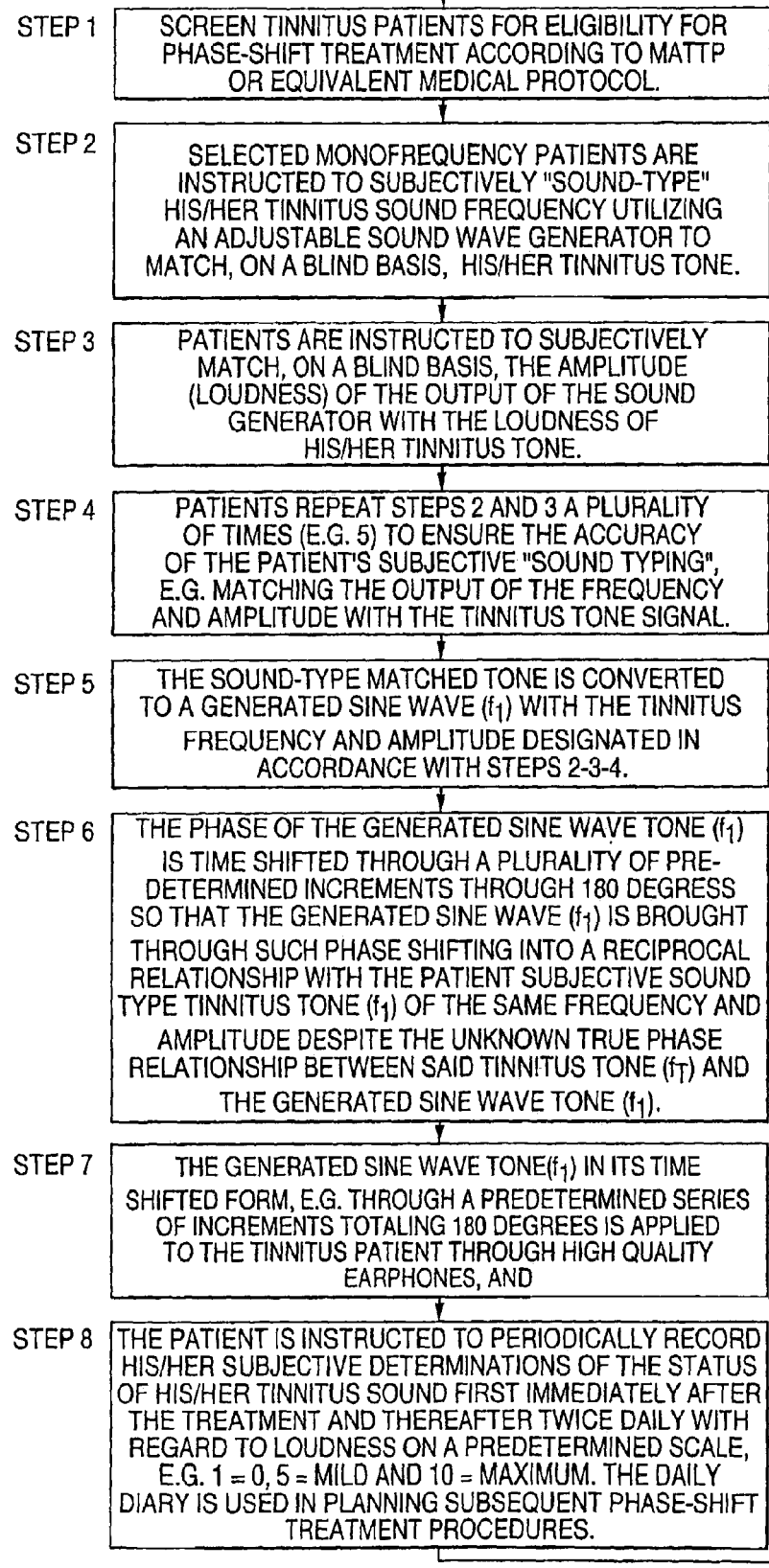

METHOD AND APPARATUS FOR TREATMENT OF MONOFREQUENCY TINNITUS UTILIZING SOUND WAVE CANCELLATION TECHNIQUES

CROSS REFERENCE TO RELATED U.S. APPLICATION

This application claims the benefit of U.S. Provisional Application No. 60/272,461 filed Mar. 2, 2001 and U.S. patent application Ser. No. 10/085,088, filed Mar. 1, 2002. These related applications are hereby incorporated herein by reference in their entireties.

TECHNICAL FIELD

Applicant's inventions are related to the treatment of tinnitus patients and more particularly to improved methods and apparatus for treatment of monofrequency tinnitus patients utilizing phase shift cancellation principles.

BACKGROUND OF THE INVENTION

Tinnitus is defined as the perception of sound by an individual when no external sound is present, and often takes the form of a hissing, ringing, roaring, chirping or clicking sound which may be intermittent or constant. According to the American Tinnitus Association, tinnitus afflicts more than 50 million Americans and more than 12 million of those suffer so severely from tinnitus that they seek medical attention and many cannot function normally on a day-to-day basis.

Tinnitus, often referred to as ringing in the ears, is estimated to be present in approximately 50% of the US population over 65 years of age. In general, tinnitus takes many and varied forms which may be related to its underlying cause. Tinnitus may be caused by or related to such diverse factors as trauma, drugs, hearing loss, the normal aging process or other unknown causes.

In 1825 Dr. Jean-Marie Gaspar Itard published a book in France titled *Maladies of the Ear* in which he stated that tinnitus is a medical problem and that most patients suffering with severe tinnitus did not respond to medical treatments available at that time and most in the medical community believe that is still true today despite major advances in the medical sciences. Itard suggested that external sounds be utilized to interfere with (masking) the tinnitus sound heard by a patient and could be relieved in some instances provided the masking sound bore some relationship to the tinnitus sound heard by the patient.

As early as 1930 Dr. R. I. Wegel published a paper entitled "A Study of Tinnitus" in which he reported his findings that tinnitus is a pathologic system but that quantitative studies had not been carried forward to a point of being useful in patient diagnosis or effective treatment. The idea of using an external sound generator to mask an obtrusive tinnitus condition dates from 1928 to a work by Drs. Jones and Knudsa although many credit Saltzman and Eisner (1947) with the first successful masking treatment for tinnitus.

During the 1960s and 1970s additional tinnitus research was conducted at a number of US medical facilities including the Oregon Hearing Research Center in Portland. The Oregon Center began as a laboratory project to study tinnitus induced in animals by drugs. According to Jack Vernor initially through incidental tinnitus patient contacts, the Oregon Center gradually shifted from an animal lab focus to tinnitus patient clinic to study tinnitus and eventually develop a tinnitus masking device. The Oregon Tinnitus Masker Study resulted in a number of patient specific device recommendations including hearing aids, tinnitus maskers (sound generators) and tinnitus instruments which combine both a hearing aid with a sound generator. Early reports of the Oregon Masker Project reported substantial success in masking treatments for tinnitus patients utilizing all three devices and initially claimed a success rate in the range of 67% for tinnitus patients who accepted the Oregon recommendation of a hearing aid and 81% of tinnitus patients who accepted the recommendation for a tinnitus masker/instrument. A report by Dr. McFadden for the Working Group 89,NRC criticizes these early success reports and states that perhaps they were misleadingly optimistic.

In reporting on patient studies at the Oregon Tinnitus Clinic, Jack Vernon, director of Oregon Hearing Research Center, stated that in patient tinnitus studies phase and tone relationships are of obvious and critical importance in tone masking of tinnitus. Vernon goes on to state that one cannot repress the idea of canceling tinnitus by a proper phase adjustment of the external tone used in masking. In commenting on Wegel's earlier tinnitus treatment findings that a slight mistuning of a masking external tone produced a beat-like sensation with the tinnitus sound, Vernon reported that in a 100 patient study he was able to detect a slight beat-like sensation in only four instances. Vernon therefore concluded that the beat-like sensation found by Wegel was most probably due to octave confusion resulting in Wegel not using a single pure tone but rather a narrow band of noise. In conclusion, Vernon observed that phase manipulation justifies further patient studies as a masking parameter for tonal tinnitus treatments. Vernon's report on possible phase manipulation for treating tinnitus patients remained unchanged from its original publication in 1991 and as included in the 1997 edition of Shulman's treatise entitled "Tinnitus Diagnosis and Treatment."

In "The Origin of Tinnitus," J. Tonndorf states that little factual information exists about the mode(s) of tinnitus generation. Even today medical approaches to identifying and treating tinnitus continue to be hampered by what little is known about the human auditory system. According to A. Shulman in his 1997 treatise "Tinnitus/Diagnosis/Treatment", attempts to understand and treat or control tinnitus are unfortunately still limited by the lack of suitable models and therefore more flexibility in thinking about and treating tinnitus will be required in order to foster the development of new medical modalities in the diagnosis, treatment and control of tinnitus. Unfortunately today many patients suffering from tinnitus are too often told by their doctors that no effective cure or treatment exists and therefore they will just have to learn to live with their affliction.

To remedy the current deficiencies in diagnosing and treating tinnitus patients and more particularly monofrequency (single tone) tinnitus, Applicant has developed a new, more efficient phase cancellation treatment process and apparatus that overcomes many of the shortcomings taught by the prior art.

There is a long-felt need for an effective treatment for monofrequency tinnitus patients to substantially reduce, relieve or eliminate the often substantially debilitating condition of tonal tinnitus.

Glossary

Amplitude—The instantaneous amplitude of an oscillating quantity (e.g. sound pressure) is its value at any instant, while the peak amplitude is the maximum value that the quantity attains. Sometimes the word peak is omitted when the meaning is clear from the context.

B ats—Periodic fluctuations that are heard when sounds of slightly different frequencies are superimposed.

Clinical types of Tinnitus—Refers to a specific entity that can be identified by clinical and laboratory means.

Combination tone—A tone perceived as a component of a complex stimulus that is not present in the sensations produced by the constituent components of the complex when they are presented alone.

Cycle—That portion of a periodic function that occurs in one period.

Dichotic—The sounds reaching the two ears are not the same.

Diotic—The sounds reaching the two ears are the same.

Frequency—For a sine wave, the frequency is the number of periods occurring in one s. The unit is cycles per second, or Hz. For a complex periodic sound, the term repetition rate is used to describe the number of periods per second (pps).

Harmonic—A harmonic is a component of a complex tone whose frequency is an integral multiple of the fundamental frequency of the complex.

Loudness—Subjective impression of the intensity of a sound, or the intensive attribute of an auditory sensation, in terms of which sounds may be ordered on a scale extending from quiet to loud.

Masking—The amount (or the process) by which the threshold of audibility for one sound is raised by the presence of another (masking) sound.

Octave—The interval between two tones when their frequencies are in the ratio 2:1.

Phas—The phase of a periodic waveform is the fractional part of a period through which the waveform has advanced, measured from some arbitrary point in time.

Pur tone—A sound wave whose instantaneous pressure variation as a function of time is a sinusoidal function. Also called a simple tone.

Sin wave, sinusoidal vibration—A waveform whose pressure variation as a function of time is a sine function. This is the function relating the sine of an angle to the size of the angle.

Ton—A sound wave capable of exciting an auditory sensation having pitch.

Wav form—The form or shape of a wave. It may be represented graphically by plotting instantaneous amplitude, pressure, or intensity as a function of time.

White noise—Broadband noise having constant energy per unit of frequency.

SUMMARY OF APPLICANT'S INVENTION

Tinnitus is often understood by a layman as a sound heard by an individual when there is no external sound present. According to the American Tinnitus Association, more than 50 million Americans suffer from tinnitus and unfortunately the cause or causes of tinnitus are not well understood by the medical community and there is currently no cure for the affliction so many tinnitus sufferers are often told by their doctor to learn to live with it.

In accordance with novel aspects of Applicant's novel apparatus and method, a monofrequency tinnitus patient is first sound-typed subjectively by the patient in terms of the frequency and amplitude (loudness) by comparing the tinnitus sound to the output of an external sound generator. The tinnitus patient adjusts the output of the sound generator until an exact match is identified and preferably this subjective sound typing is repeated a number of times in a blind manner, i.e. the patient during the sound-typing process does not see the frequency and amplitude displays of the sound generator. Based upon the sound-typing data, an external sound generator generates a sinusoidal tone equal in frequency and amplitude to the patient's monofrequency tinnitus sound and this externally generated tone is then phase shifted in a step-wise fashion or alternatively in a direct single motion through at least 180 degrees whereby the generated tone is phase shifted relative to an arbitrary point through a reciprocal relationship with the patient's tinnitus tone and the shifted sound wave is applied to the patient via high quality earphones thereby effecting a cancellation or a substantial diminishment of the patient's tinnitus tone.

BRIEF DESCRIPTION OF THE DRAWINGS

FIG. 1 is a block diagram of monofrequency tinnitus treatment apparatus in accordance with aspects of Applicant's invention.

FIG. 2 is a series of sine waves which graphically illustrate phase shift cancellation principles in accordance with further aspects of Applicant's invention, and FIG. 3 is a logic flow diagram illustrating one of Applicant's preferred sequence of steps to implement Applicant's phase shift process for treatment of monofrequency (pure tone) tinnitus patients.

DETAILED DESCRIPTION OF PREFERRED EMBODIMENTS

Referring now to FIG. 1, the preferred embodiment of apparatus for Applicant's novel phase shift treatment of monofrequency tinnitus patients is illustrated in block diagram form. A sound generator 10, which may be an Agilent model 33120A function generator or any equivalent commercially available wave form generator, is coupled to a patient's headset 12 and to an input of an oscilloscope 14 which may, for example, be of the type commercially available in the U.S. from Tektronics, Inc. A second sound generator 16 is also coupled to another input of oscilloscope 14.

Sound generator 10 has a plurality of adjustable knobs 18, 20 and 22 and an output terminal 24. As will be hereinafter explained in further detail particularly with respect to FIG. 3, a monofrequency tinnitus patient is asked to adjust knobs 18 and 20 of sound generator 10 until the output of the sound generator applied to headphones 12 matches the tinnitus monofrequency tone heard by the patient. This subjective "sound-typing" is preferably repeated a plurality of times on a blind basis, i.e. the patient cannot see the readout display, not shown, on the sound generator and the subjective sound typing data for each of the self-typing steps is recorded by an attending audiologist or physician.

The principles of sound wave cancellation by superimposing, e.g. summing, a second sine wave having the same frequency and amplitude, as the first sine wave with a phase shift of 180 degrees is well understood in the electrical and measurement arts and is utilized in many technical fields including audiology, mechanics and electronics generally. To prove the phase shift cancellation effect of summing two waves of the same frequency and amplitude but without any knowledge of the phase relationship of the first wave to the second wave relative to a common point, can be illustrated as follows. Sound generator 10 is set to a first tone having a frequency of f and an amplitude of A (for example in milli volts as displayed on sound generator 10) and connected to the first input of multi-beam oscilloscope 14. A second generator 16 is also set to the same tone of f with a like amplitude and the output is connected as a second input to oscilloscope 14.

With reference to FIG. 2 it may be seen that by adjusting the phase of sinewave $f_1$ through a series of steps, illustrated as $f_2 \ldots f_n$, the sum of $f_1$ plus $f_n$ neutralizes or cancels and as illustrated $f_1$ plus $f_n$ cancel when $f_n$ is 180 degrees out of phase with $f_1$. Unfortunately for tinnitus patients, the structure and operation of the human auditory system is much more complex than the simple addition of two tonal sound waves as illustrated above on a multi-trace oscilloscope 14.

It is well understood in the field of audiology that humans and animals can determine, to a considerable degree of precision, the direction of a sound wave remote from them and to some extent can estimate the distance of a sound source from an observer. Numerous experiments in the field of audiology have attempted to analyze the mechanics by which so-called binaural localization is accomplished in humans and animals. There are two primary factors which assist one in determining the direction of an arriving sound: (1) relative intensity in the hearer's two ears and (2) the difference in phase between the ears or for a sinusoidal tone, the difference in phase between the sound waves arriving at the right and left ear of the hearer respectively. Thus it is clear that a human or animal auditory system can distinguish phase shifts of complex sound signals and for pure or monofrequency tones specifically. This type of auditory analysis is frequency dependent and for frequencies above 1 K hertz most observers tend to determine the direction of a sound source from the side of the ear receiving the louder sound. Thus in general it appears that auditory localization by phase difference is most definite for a band of frequencies in the order of 1 to 51 K hertz. As discussed hereinafter with reference to FIG. 3, in implementing tinnitus treatments it is important to determine not only the tonal quality of the tinnitus signal but whether the tinnitus patient hears his/her tinnitus in both ears, in only one ear or as many patients indicate when asked where they hear the tinnitus they respond in their head without reference to either their right or left ear.

Referring again to FIG. 1, the structure and operation of Applicant's preferred embodiment of apparatus for treating monofrequency tinnitus patients will be further described. A phase shift network 30 may be of any type known to those skilled in the auditory and electrical arts. Applicant's preferred embodiment of sound generator 10 is of the type commercially available from Agilent as model 3312A function generator, which incorporates an output waveform phase shift feature. To select the waveform phase shift feature, an operator may dial in the desired phase shift (scaled in degrees) by turning knob 22 to the appropriate phase shift factor, e.g. 10 degrees, 20 degrees etc. which affects the desired shifts, e.g. of delta 1, delta 2, etc. as shown in FIG. 2.

As shown in FIG. 1, a gang switch 32 in its position illustrated connects the output of sound generator 10 to the patient's headphones 12, which preferably is a high quality headset commercially available e.g. from Bose, Inc. of Massachusetts, USA under the trademark QuietComfort. If the sound generator 10 does not have a phase shift feature, a separate phase shift network 30 of any known type may be utilized. Switch 32, as illustrated, applies the shifted output of sound generator 10 via phase shift network 30 to headphones 12. Then the successively phase shifted increments of sinewave tone from generator 10, as herein-above explained, successively shifts the generated sine wave relative to f, as illustrated in FIG. 2, to accomplish the reciprocal 180 degree phase canceling relationship through the steps illustrated as $f_1 \; f_2 \ldots f_n$.

Referring again to FIG. 1, a further direct or essentially one step phase-shift reciprocal cancellation embodiment of Applicant's improved apparatus and method for treating monofrequency tinnitus patients will be described. The patient sound-typing is accomplished, as hereinabove described, by adjusting the frequency and amplitude knobs 18-2 and 20-2 of sound generator 16 until the desired match with the patient's tinnitus tone and amplitude are achieved. Then, as in the previously described embodiments disclosed above, the like frequency and amplitude knobs 18 and 20 of sound generator 10 are set to like settings of generator 16 and the phase shift knob 22 of sound generator 10 is adjusted in a direct or essentially one step motion to bring the output wave form of sound generator 10, which is also applied to oscilloscope 14, into a phase shift, reciprocal, canceling relationship of 180 degrees relative to the output wave form of sound generator 16 which is also displayed on oscilloscope 14. As hereinabove described with reference to FIG. 2, this phase canceling reciprocal wave form relationship with regard to the respective outputs of sound generators 10 and 16 is depicted as the sum of $f_1 + f_n$ which verifies the identical match between the generated treatment tone of sound generator 10 and the patient selected tinnitus tone. As hereinabove explained with relation to the previous described embodiments, the phase shifted output of signal generator 16 is directly applied to the tinnitus patient via headphones 12 preferably for a time period in the order of ten minutes for each patient treatment. In this alternative embodiment, switch 32 remains in the position indicated in FIG. 1 as the phase shift network is not utilized. However phase shift network 30 and switch 32 may be utilized to effect a 180 degree shift of generator 10 output in lieu of the phase shift adjustment described above utilizing knob 22 of sound generator 10.

Referring now to FIG. 3, there is illustrated in a logic flow diagram one of Applicant's preferred sequence of steps to accomplish Applicant's phase shift treatment for monofrequency tinnitus patients. In Step 1 a patient's eligibility for the phase shift treatment is determined in a medical-audiologic tinnitus patient protocol (MATPP) or similar medical protocol. The medical-audiologic examination determines if Applicant's phase shift treatment is appropriate for the patient and what if any cause can be ascribed for a particular patients condition. As is known to those skilled in the Tinnitus Medical and Audiologic Arts, tinnitus classification generally employs four major factors: (1) localization, (2) intensity, (3) sound types or composition, i.e. pure tone or complex tones, and (4) temporal variability of the tone(s). At present only pure tone, non-drug induced monofrequency tinnitus appears appropriate for this first evolution of Applicant's phase shift tinnitus treatment program. For a more complete understanding of MATPP see "Medical-Audiologic Tinnitus Patient Protocol" in Shulman, Chapter 15.

Steps 2, 3 and 4 provide for the subjective "sound-typing" by the patient which generally involves matching the output of an external sound wave generator to the tone (frequency) and amplitude (loudness) to his/her monofrequency tinnitus tone. In accordance with Applicant's preferred embodiment, this patient subjective "sound-typing" is accomplished in a soundproof environment illustrated as movable member 36 in FIG. 1, in a sequence of at least five sequential trials, each on a blind basis, where the patient is not able to determine visually the output of the sound generator by viewing any of the dials or displays on the sound generator 10. If there are any major differences in the multiple "sound-typing" steps further tests are conducted to ensure octave confusion or other errors by the patient are not involved.

In Step 5, utilizing the subjective patient data from Steps 2, 3 and 4, a pure tone sinusoidal wave form from the external sound generator is generated which is substantially identical to the patient's tinnitus tone in both amplitude and frequency.

In Steps 6 and 7, the generated sinusoidal wave form is sequentially phase shifted through a series of steps a predetermined amount (delta 1, delta 2 . . . delta n as shown in FIG. 2.). Where the predetermined phase shift increments add up to at least 180 degree phase shift relative to an arbitrary reference and where the generated tone and the patient's tinnitus tone are the same frequency and amplitude, the generated tone is brought into a reciprocal, cancellation relationship with the patient's tinnitus tone. This sequential phase shift iteration is useful and indeed necessary in practicing this embodiment of Applicant's sequented step phase cancellation treatment because at present there are no instrumentation processes to directly measure the phase relationship between a patient's monofrequency tinnitus tone and the externally generated sinusoidal tone. However the incremental 180 degree shift brings the generated sound wave at some point into a reciprocal relationship (i.e. canceling) relative to the patient's tinnitus tone.

In the alternative direct or essentially one step embodiment described above, there is no need for the sequential or incremental phase shift steps described in Steps 6 and 7 of FIG. 3 as the desired phase shift of 180 degrees is implemented directly or in essentially one motion by using the phase shift feature of sound generator 10. As previously described, the respective output wave forms of sound generators 10 and 16 may be algebraically added or summed to produce wave form or tone cancellation as shown in FIG. 2. Such total tone cancellation feature of this embodiment is significant for Applicant's improved monofrequency tinnitus patient treatment because it conveniently verifies the identical match between the treatment tone and amplitude with the subjective patient determined tinnitus tone and amplitude or loudness which has been found to be useful. Thus in lieu of the sequential, phase shift steps described in Steps 6 and 7 of FIG. 3, in this alternative embodiment the output wave form of sound generator 10 is directly shifted through 180 degrees to bring it into phase canceling, reciprocal relationship with the output of sound generator 16 and the phase shifted output wave form of sound generator 10 is then applied to the tinnitus patient directly via headphones 12 for a predetermined time period preferably in the order of ten minutes per treatment.

The phase shift of the generated wave form is preferably accomplished utilizing a phase shift feature of the Agilent sound generator 10, as hereinabove described. Alternatively the sequential or direct phase shift of the generated wave form may be accomplished in a phase shift network 32 which as described above the output of which may be selectively coupled to the patient's headset 12 via switch 32. In either instance, these phase shift increments or direct phase shift step may be manually selected by the attending audiologist/physician or it may be automated using an appropriate timing circuit, not shown, in conjunction with the phase shift network 32. In either event within Applicant's preferred embodiment, each increment or direct step of the phase shifted wave form is preferably coupled to the patient's headset 12 for a period in the order of 10 minutes and in utilizing the incremental steps each incremental phase shift is in the order of 20 degrees whereby a patient treatment for the full 180 degree shift would be, in the order of 90 minutes. For the direct step phase shift embodiment, the shifted waveform is likewise coupled to the patient's auditory system for a predetermined period of time, preferably ten minutes.

Step 8 is intended to enable the attending physician and the patient to subjectively evaluate the effectiveness of a phase shift treatment in minimizing or alleviating entirely the deleterious patient tinnitus condition. A patient diary is preferably kept to record data at predetermined intervals after a phase shift treatment is completed and thereafter at several daily intervals before the next treatment. The diary should record patients subjective data regarding the loudness of his/her tinnitus tone (e.g. on a 1-10 scale where 1=0 or negligible loudness, 5=intermediate loudness and 10=very loud. Preferably the patient diary additionally includes data regarding: 1) where does your tinnitus tone appear to be located? 2) if more than one location, which location is worse? 3) has your tinnitus tone changed appreciably or does it appear to be more than one tone? and 4) does the location of your tinnitus tone tend to fluctuate in tone or loudness? Data from the patient's diary is useful in planning subsequent patient treatment routines and schedules.

Referring now to Table 1 below, the subjective, patient determined data for a monofrequency tinnitus phase shift patient treatment study for twenty-three patients is reported. Table 1 reports on a clinical single blind study which was conducted in New York under the direction and control of Applicant.

A brief description of the study methodology hopefully will set the stage to more fully understand the data reported in Table 1. Patient volunteers with monofrequency tinnitus only were selected through responses to newspaper advertisements. Each patient completed a consent form agreeing to come to the designated office once a week for eight weeks to participate in a single blind study in which 50% of the study group would initially receive Applicant's sound cancellation tinnitus treatments and the other 50% would initially receive a placebo or sham treatment. After four weeks there would be a cross-over, i.e. the sham treatment group would begin receiving Applicant's sound cancellation treatments and the previously treated group would receive during the same period only sham treatments.

Each patient was asked to keep a daily tinnitus diary or log of his/her subjective estimate of tinnitus intensity on a scale of 1-10, with 10 being the patient's own usual level of tinnitus tone and 1 being minimal or negligible tinnitus tone intensity. Each patient was asked to make recordings daily at 0800 and 1600 hours respectively. At the initial screening session, a relevant patient medical history was obtained and the program methodologies were fully explained. At each weekly treatment session, each patient was asked to deliver their respective diaries to a program staff assistant, but they were not shown or discussed with the physician or audiologist administering the test or to Applicant.

Each patient was "sound-typed" as hereinabove explained in connection with FIG. 3 with each patient manipulating an adjustable frequency (tone) dial on an Agilent 33250a generator or its commercial equivalent. Each patient then similarly determined the amplitude or loudness of his/her tinnitus tone. These steps were repeated a number of times to ensure the accuracy of a patient's sound typing data and tests were repeated if a particular patient's results varied from try to try by more than 10% until exact determinations were assured. Care was taken to avoid octave confusion where sound typing may result in a frequency which is a multiple or submultiple of the actual tinnitus tone.

Applicant's frequency cancellation tinnitus treatment began with the patient's sound type data being set up on a first sound generator and like tone and amplitude data then set up on a second sound generator (see FIG. 1, sound generators 16 and 10 respectively) and the output wave forms from sound generators 16 and 10 coupled as inputs to an oscilloscope 14. With identical wave forms from sound generators 16 and 10 displayed on the oscilloscope 14, the phase shift knob 20 of sound generator 10 is utilized to shift the phase of output wave form of sound generator 10 directly or essentially in a single continuous movement into a reciprocal, 180 degree relationship with the output of sound generator 16. By summing the output wave forms from sound generator 16 and the phase shifted tone output from sound generator 10, the phase shifted reciprocal relationship of the two wave forms (See FIG. 2) can be observed and then the phase shifted wave form from sound generator 10 is also sent to the patient's auditory system via headphones 12 for a treatment period of 10 minutes. For the placebo or control group treatments, the sound wave was not phase shifted but set at a steady level of 100 hertz at 50 milivolts for a treatment period of 10 minutes. At the beginning and end of each treatment session, the patient's tinnitus tone amplitude was again subjectively determined, as hereinabove described.

To simplify summary study data entry in Table 1, the following conventions were utilized to characterize each patient's subjective tinnitus status which were then combined following completion of the eight weekly treatments into the following categories: 1=Excellent—complete or near complete relief with loudness reduction of 90% or more; 2=Very Good—strong partial relief response in the order of 75% loudness reduction; 3=Good—partial relief response in the order of 50% loudness reduction; 4=Fair—partial relief in the order of 25% loudness reduction; and 5=Poor—minimal or no relief from original tinnitus condition.

Referring now to Table 1, as is shown of the twenty-three treated patients, seven patients experienced complete or nearly complete relief (1 s); four patients experienced strong partial relief (2s) with loudness reduced in the order of 75%; eight patients experienced good partial relief (3s) with loudness reduced in the order of 50%; one patient experienced partial relief with loudness reduced in the order of 25% (4); and three patients experienced no or negligible relief from their original tinnitus condition (5s). None of the patients experienced any increase or aggravation of his/her original tinnitus condition. As shown, the study encompassed a wide range of tinnitus tone levels and a wide range of individuals who had suffered from tinnitus for many years.

It is important in evaluating the Table 1 data to recognize that the response of all of the placebo or control patients was a #5—minimal or no relief response from their respective original monofrequency tinnitus condition (5s). When compared to the nineteen responses in the treated patient group of twenty-three patients, it is statistically very significant and yields a p-value of p=0.001.

As is well known in the medical arts, tinnitus has many different forms and different causes. A survey of medical tinnitus treatment literature clearly demonstrates how difficult a problem treating tinnitus patients truly has been over the years and that there is currently no known cure for tinnitus. Vernon has recently reported in 1998 that early optimistic reports of tinnitus cures in the order of 80% are in drastic contrast to more humble results from various other recent clinical experiences. However, for those who suffer substantial medical disability from tinnitus, any, even temporary relief can be significant even if their tinnitus is not completely or permanently cured. The data of Table 1 demonstrates that a total of nineteen treated patients (82%) achieved at least a 50% reduction in their tinnitus loudness and more than 30% reported complete or nearly complete (more than 90% loudness reduction) relief.

While the tinnitus patient treatment study reported in Table 1 utilized primarily the embodiment of Applicant's improved treatment apparatus and methods which utilizes direct or one-step phase shift cancellation adjustments, the other sequential, incremental-step phase shift adjustments embodiments are equally applicable and additional studies are and will be directed to those other embodiments of Applicant's inventions as distinctly claimed in the appended claims.

TABLE 1

Tinnitus Phase-Shift Cancellation Treatment
Clinical Single Blind Study

| Patient # | Age | Years | Subjective Tone Classification (mhz/milivolts) | Subjective Status After Treatment |
|---|---|---|---|---|
| 1 | 50 | 17 | 11.7/1000 | 1 |
| 2 | 67 | 59 | 0.20/100 | 1 |
| 3 | 72 | 15 | 3.60/272 | 1 |
| 4 | 66 | 2.5 | 6.50/110 | 1 |
| 5 | 64 | 4 | 2.40/117 | 1 |
| 6 | 55 | 4 | 4.40/50 | 1 |
| 7 | 48 | 10 | 6.31/102 | 1 |
| 8 | 60 | 6 | 1.60/107 | 2 |
| 9 | 66 | 2 | 3.40/70 | 2 |
| 10 | 30 | 2 | 2.38/50 | 2 |
| 11 | 49 | 15 | 3.02/96 | 2 |
| 12 | 73 | 35 | 0.833/62 | 3 |
| 13 | 66 | 7 | 0.100/126 | 3 |
| 14 | 65 | 15 | 0.10/84 | 3 |
| 15 | 52 | 27 | 5.50/50 | 3 |
| 16 | 73 | 5 | 0.100/73 | 3 |
| 17 | 57 | 21 | 1.93/50 | 3 |
| 18 | 84 | 15 | 3.70/84 | 3 |
| 19 | 67 | 5.5 | 0.100/86 | 3 |
| 20 | 53 | 10 | 6.00/10 | 4 |
| 21 | 63 | 15 | 0.64/90 | 5 |
| 22 | 54 | 6 | 2.20/30 | 5 |
| 23 | 56 | 2.5 | 8.10/35 | 5 |

While Applicant's improved apparatus and methods for treating monofrequency tinnitus patients utilizing phase-shift cancellation principles have been described in connection with several specific embodiments thereof, it is to be understood that these embodiments are by way of illustration and not of limitation, and therefore the scope of the appended claims of Applicant's novel inventions are to be construed and interpreted as broadly as the relevant prior art will permit.

What is claimed is:

1. Apparatus for treating tinnitus sufferers comprising
a portable record member,
at least one audio recording track on said record member,
a succession of signal recordings in said at least one recording track all at a predetermined audio frequency, the recordings being in a phase shift sequence, such that the successive signal recordings are at successive phase shifts and each occupies a predetermined time along the recording track, the sum of the phase shifts occupying at least a half wavelength at said predetermined frequency.

2. Apparatus as in claim 1 wherein
the portable record member includes perturbations that record the predetermined frequency at a predetermined amplitude, and the succession of signal recordings, at least a majority of which are at a different phase angle than the others.

3. Apparatus as in claim 1 wherein each signal recording is recorded for a predetermined length of the recording track.

4. Apparatus as in claim 3 wherein each signal recording is recorded for a same length of the recording track.

5. Apparatus as in claim 4 wherein at least nine equal length signal recordings at different phases are recorded over a period of a half wavelength at the predetermined frequency.

6. Apparatus as in claim 4 wherein at least thirty signal recordings at different phases are recorded over a period of a half wavelength at the predetermined frequency.

7. Apparatus for treating tinnitus comprising
first means for applying to a tinnitus sufferer a first sound at a selected frequency,
second means for thereafter applying to the tinnitus sufferer a succession of additional sounds at the selected frequency, each such additional sound being phase shifted with respect to a prior sound in the succession, wherein phases of said succession of sounds are incrementally spaced over at least a half wavelength of the selected frequency.

8. Apparatus as in claim 7 comprising means for applying sounds over a range of frequencies to said tinnitus sufferer so tat said tinnitus sufferer can determine the selected frequency as corresponding to tinnitus symptoms of that tinnitus sufferer.

9. Apparatus for treating tinnitus comprising
a sound generator for producing sound at a selected audio frequency, and amplitude, and
a phase shift network for shifting the phase of the produced sound at regular intervals, so that the sound is at one phase for a selected time period, and then shifts in phase for each of successive intervals thereafter.

10. The apparatus in claim 9 further comprising
a transducer for receiving the output signals from the sound generator and applying them to a tinnitus sufferer.

11. The apparatus in claim 9 wherein the phase shift network shifts the phase in equal increments at least nine times over a half wavelength of the selected audio frequency.

12. The apparatus in claim 9 wherein the phase shift network changes the phase about every ten minutes.

13. The apparatus in claim 9 wherein the phase shift network shifts the phase in equal increments at least thirty times over about a half wavelength of the selected audio frequency.

14. The apparatus in claim 13 wherein the phase shift network changes the phase about every minute.

* * * * *

UNITED STATES PATENT AND TRADEMARK OFFICE
CERTIFICATE OF CORRECTION

| | | |
|---|---|---|
| PATENT NO. | : 7,347,827 B2 | Page 1 of 1 |
| APPLICATION NO. | : 10/622183 | |
| DATED | : March 25, 2008 | |
| INVENTOR(S) | : Daniel S. J. Choy | |

It is certified that error appears in the above-identified patent and that said Letters Patent is hereby corrected as shown below:

Column 12, Line 1, Claim 8, change "so tat said tinnitus sufferer" to --so that said tinnitus sufferer--

Signed and Sealed this

Seventeenth Day of June, 2008

JON W. DUDAS
*Director of the United States Patent and Trademark Office*